(12) United States Patent
Habibi-Naini et al.

(10) Patent No.: US 9,138,045 B2
(45) Date of Patent: Sep. 22, 2015

(54) INTERNALLY FED APPLICATOR

(75) Inventors: Sasan Habibi-Naini, Rikon (CH); Josef Ettlin, Eichberg (CH)

(73) Assignee: Sulzer Mixpac AG, Haag (CH)

( * ) Notice: Subject to any disclaimer, the term of this patent is extended or adjusted under 35 U.S.C. 154(b) by 380 days.

(21) Appl. No.: 13/295,603

(22) Filed: Nov. 14, 2011

(65) Prior Publication Data

US 2012/0134738 A1     May 31, 2012

(30) Foreign Application Priority Data

Nov. 26, 2010    (EP) ..................................... 10192699

(51) Int. Cl.
| | | |
|---|---|---|
| A47L 13/22 | (2006.01) | |
| A46B 11/00 | (2006.01) | |
| A61C 19/06 | (2006.01) | |

(52) U.S. Cl.
CPC ............. A46B 11/00 (2013.01); A46B 11/0072 (2013.01); A61C 19/06 (2013.01); A46B 2200/1066 (2013.01); A61C 19/066 (2013.01)

(58) Field of Classification Search
CPC ....... A61C 3/005; A61C 19/063; A46B 11/06
USPC ............... 401/289, 282, 284, 286; 433/87, 89
See application file for complete search history.

(56) References Cited

U.S. PATENT DOCUMENTS

| | | | | |
|---|---|---|---|---|
| 1,606,537 | A * | 11/1926 | Sevier ............................ | 401/288 |
| 3,418,054 | A * | 12/1968 | Kirch ......................... | 401/188 R |
| 4,619,009 | A * | 10/1986 | Rosenstatter ..................... | 15/29 |
| 5,098,291 | A | 3/1992 | Curtis et al. | |
| 5,398,365 | A * | 3/1995 | MacKenzie ...................... | 15/160 |
| 5,816,804 | A * | 10/1998 | Fischer ............................ | 433/90 |
| 6,382,972 | B1 * | 5/2002 | Fischer et al. ................... | 433/90 |
| 6,450,810 | B1 * | 9/2002 | Fischer et al. ................... | 433/80 |
| 7,213,998 | B2 * | 5/2007 | Hay .............................. | 401/289 |
| 7,476,049 | B2 * | 1/2009 | Jensen .......................... | 401/288 |
| 2008/0095571 | A1 * | 4/2008 | Geigle .......................... | 401/289 |
| 2009/0123217 | A1 | 5/2009 | Ross | |

FOREIGN PATENT DOCUMENTS

| | | |
|---|---|---|
| DE | 20114390 | 1/2003 |
| EP | 0278828 | 8/1988 |
| EP | 0945368 | 9/1999 |
| WO | WO 2007073917 | 7/2007 |
| WO | WO 2009100285 | 8/2009 |

OTHER PUBLICATIONS

European Search Report for European Patent Application No. 10192699.6 mailed on May 17, 2011.

* cited by examiner

*Primary Examiner* — Jennifer C Chiang
(74) *Attorney, Agent, or Firm* — Global IP Counselors, LLP

(57) ABSTRACT

An internally fed applicator for applying a fluid is provided having a closure piece for a preferable locking fixing of the applicator of a dispensing apparatus and having an internally hollow lip section connected to the closure piece in a fluid conducting manner, which lip section has, at least one of its borders which bound its free outlet, a bristle stock made of bristles injection molded at the lip section each having a diameter of ≤0.8 mm to which bristle stock the supplied fluid is delivered via the lip section.

30 Claims, 6 Drawing Sheets

Figures 4, 5:
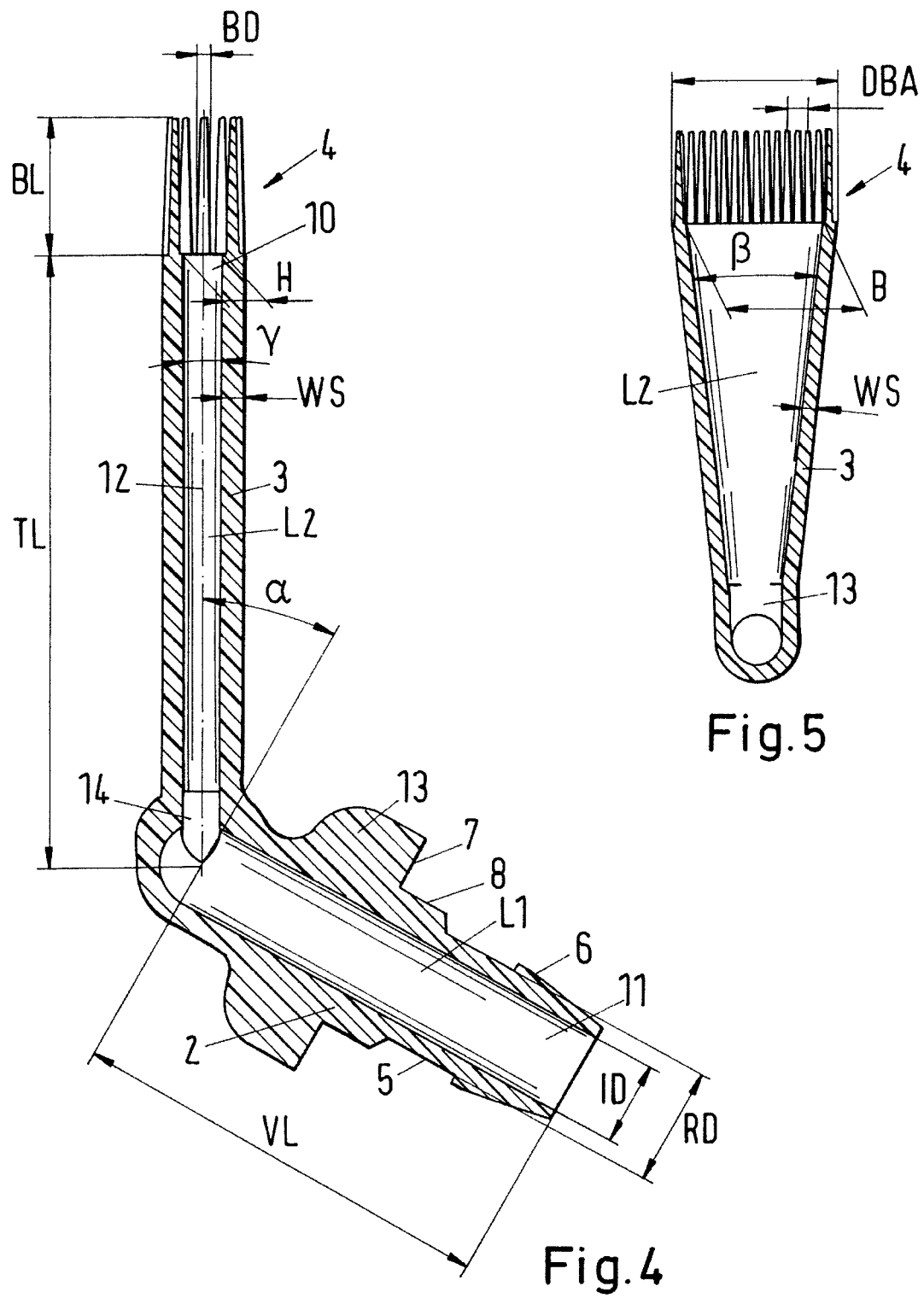

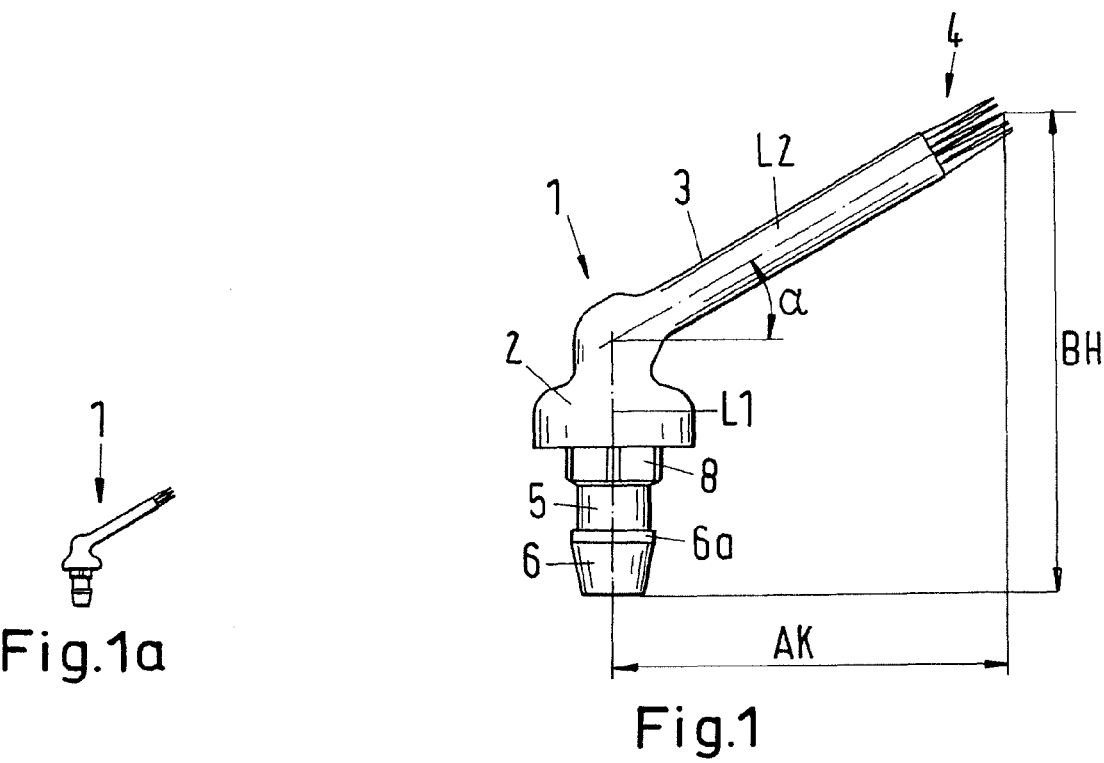
Fig. 1a
Fig. 1
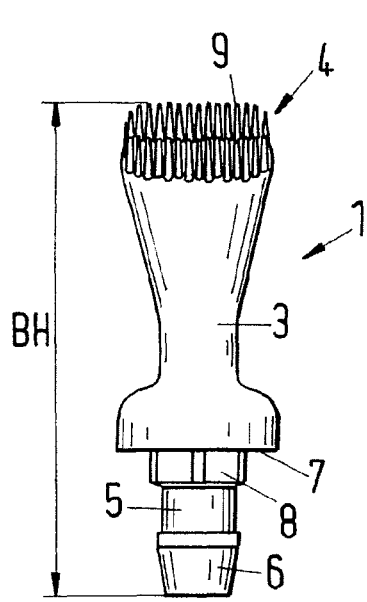
Fig. 2
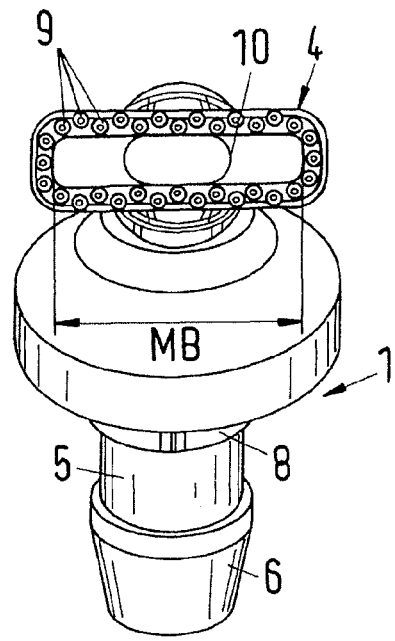
Fig. 3

INTERNALLY FED APPLICATOR

PRIORITY CLAIM

The present application claims priority to European Patent Application No. 10192699.6 filed on Nov. 26, 2010, the disclosures of which are incorporated herein by reference.

The invention relates to an internally fed applicator for dispensing a fluid in accordance with the preamble of the independent patent claim.

Internally fed applicators are used, for example, in the field of dentistry, to dispense flowable substances onto the teeth of a patient. This can, for example, be a bleaching substance by means of which the teeth are made white, a substance for professional fluorination of the teeth or an impression material with which precise impressions of teeth or dental sections can be produced. Hereby so-called one component systems exist in which the fluid to be dispensed only comprises a single component, or two or multi component systems exist in which the fluid to be dispensed includes two or more substances which are brought into contact with one another and mixed just before the application. The component and/or the components are typically provided in one or more supply chambers of a dispensing apparatus and are then dispensed for the application. Examples of such dispensing apparatuses are needles or double-needles.

In the case of only one component the dispensing apparatus typically has a nozzle, a lip or a needle via which the fluid is dispensed. In the case of two or more components the dispensing apparatus has a static mixer, typically designed tube-shaped, whose inlet is connected to the supply chambers so that the different components can arrive from the supply chambers in the static mixer where they are mixed to a homogeneous substance on flowing through the static mixer which then exits the mixer at the outlet for application.

In this respect it is frequently the case that the outlet of the mixer or of the nozzle is to coarse to allow a specific and precise application of the previously mentioned applications. For this reason applicators are known, for example, wide slot nozzles which are placed at the outlet of the mixer and/or the nozzle or the needle as so-called intra oral tips (IOT) to enable a more precise application.

A different case of application, for which the aforementioned is true in a literal sense, is/are one component or multi-component glues which have to be applied very precisely.

Even if such applicators, which are placed at the outlet of a mixer or a nozzle, have been tried and tested in practice for many applications there is still the need for improvement. For example, e.g. on bleaching of teeth or on the fluorination of teeth it is desirable to dispense the fluid to be applied very homogeneously and aerially as a thin layer onto a predefined surface. In this respect a selective dispensing which is as thin as possible is also frequently crucial. However, this can only be realized to a certain extent with the known applicators, such as wide slit nozzles. As a rule further working steps are subsequently required to enable a homogeneous aerial dispensing.

Starting from this prior art it is therefore an object of the invention to provide an applicator for dispensing a fluid which enables a comfortable, fast, fine, uniform and clean areal dispensing of a fluid, for example in the field of dentistry or on bonding. The subject matter of the invention satisfying this object is characterized by the features of the independent patent claim.

Thus, an internally fed applicator for dispensing a fluid is provided in accordance with the invention, having a closure piece for a preferably locking fixing of the applicator of a dispensing apparatus and having an internally hollow lip section connected to the closure piece in a fluid conducting manner, which lip section has, at least one of its borders which bounds as its free outlet, a bristle stock made of bristles injection molded at the lip section each having a diameter of at most 0.8 mm to which bristle stock the supplied fluid is delivered via the lip section.

The invention is suitable, in particular for non-cosmetic fluids. In this respect the term "non-cosmetic fluids" means such fluids which are not intended for the application of a cosmetic onto skin or into hair. Non-cosmetic fluids in the sense of the present application are, in particular such fluids for dental applications such as impression materials, bleaching substances or substances for the fluorination of teeth or substances for different treatments of the teeth or the gums, as well as glues, in particular for industrial or medical applications (tissue adhesives) or for handyman applications.

The bristles of the bristle stock provided in accordance with the invention are in this respect exceptionally fine as they only have a diameter of at most 0.8 mm. Preferably the diameter is even smaller and amounts to at most 0.5 mm and in the ideal case to even at most 0.35 mm.

Insofar as one talks of a bristle diameter one assumes that the bristles are substantially round in cross-section (apart from deviations due to tolerance). From a process engineering point of view the use of substantially round bristles is the simplest case and is therefore preferred. In accordance with the invention, however, for example also oval and/or elliptical bristles can be used or even other profiled bristles. For example, such which have an X-shaped cross-section. The bristle diameter stated is then understood to be a mean diameter, this means as the diameter of that circle whose area corresponds to the cross-sectional area of the corresponding bristle profile, for example the X-shaped bristle profile.

Normally, the applicators in accordance with the invention are one-way applicators which are disposed of together with the part of the dispensing apparatus to which they are connected, i.e. for example a lip or a mixer following the application.

The fine bristles are preferably injection-molded and are ideally sprayed in one step with the lip section.

Preferably the bristle stock completely surrounds the outlet. It is hereby prevented that on awkward handling fluid possibly drops of as it flows past the bristles.

In the scope of a preferred embodiment it is provided that the predominant number of bristles forming the bristle stock and preferably all bristles have a bristle center line which extends essentially in parallel to the center line of the lip section. Such bristles enable an ideal application behavior and cause the least difficulties on manufacture of the lip section.

The same is true for the preferred embodiment which provides that the bristles preferably do not protrude or at least do not substantially protrude into or in front of the exit cross-section of the outlet of the lip section.

Preferably at least one of the borders, at best, however, all borders, respectively only have a single row of bristles standing adjacent one another along the respective border. The limitation to single bristle rows allows to keep the applicator exceptionally fine which has advantages from an application point of view when, for example, a tooth or the denture should be worked on therewith.

However, also such applicators fall within the scope of this invention, in which at least one of the boundaries, however, at best all of the boundaries are not only occupied with a single row of bristles respectively standing along the respective border next to one another, but that up to three of such rows of bristles stand parallel to one another along the respective border. However, such embodiments are not preferred as these are basically inferior embodiments, at least when a multi-row is not only provided locally.

In the scope of a preferred embodiment it is provided that the predominant number of bristles and preferably all of the bristles have a bristle length of at most 5.5 mm, preferably of at most 4.5 mm, particularly preferably at most 3.5 mm and ideally of at most 2.8 mm. It has surprisingly been found that such short bristles are not inferior with regard to their effectivity on dispensing than longer bristles. However, the shorter bristles are more durable, in particular when these are injection-molded bristles. As longer bristles are easily overloaded on dispensing and then, at least when a certain fatigue is present, are permanently bent so that they protrude omnidirectional. This not only imparts an unsightly look to the applicator but also degrades the dispensing behavior. Furthermore, the shorter bristles are more simple to manufacture during injection molding, as with an increased bristle length the danger increases that a demolition of a number of bristles takes place on formation of the bristles which then leads to a qualitatively deteriorated appearance.

In the scope of a different preferred embodiment it is provided that the bristle diameter at the bristle root is smaller than the wall thickness of the wall carrying the bristles in the region of the bristle root. Ideally the bristle diameter is at least 30% smaller than the wall thickness of the wall supporting the bristles. Such a design enables a secure attachment of the bristles at the wall supporting the bristles, in particular for injection molded bristles. In this respect a good moldability is also ensured by such a design.

On the other hand, it is also advantageous when the wall thickness of the wall supporting the bristle is merely as thick as the wall thickness is approximately in the region of the bristle diameter at the bristle root. On very generous consideration this is the case when the wall thickness is at most 3 times the bristle diameter at the bristle root. Preferably, the wall thickness is smaller and is merely at most the 2-fold and ideally even at most the 1,5-fold of the bristle diameter at the bristle root.

In the scope of a different preferred embodiment it is provided that the bristles are respectively only arranged in a single row along the respective boundary, however, that a certain displacement is provided between neighboring bristles so that, for example, a second bristle neighboring the first bristle is respectively displaced by at least ⅓ of the bristle diameter in a direction transverse to the run of the wall with regard to the first bristle.

It is advantageous, for a fine dispensing, for certain few fluids when the field of bristles preferably includes more than 18 bristles, especially more than 26 bristles. The required accuracy of dispensing is thereby ensured for all fields of application for an applicator having such a minimum number of bristles. It is true that in the case of doubt thinner bristles are preferably to be provided and in return a larger number of bristles.

However, from a point of view of manufacturing it makes no sense to keep the number of bristles of the applicator in accordance with the invention arbitrarily large. For this reason, the field of bristles for a preferred embodiment includes less than 90 bristles and preferably includes less than 60 bristles. In many cases it is sensible to provide less than 45 or 44 bristles.

In the scope of a preferred embodiment it is provided that the diameter and/or the width of the lip section increases at least in one plane from the closure piece to its free outlet.

Hereby a relatively good metering of the fluid is ensured, as the increasing lip section is, if necessary, in the position to also take up a large amount of the cosmetic pressed through the narrowest point of the lip section and as such to "intermittently store" the pressed cosmetic. Moreover, advantages from a manufacturing point of view arise because of this. In this sense a different preferred embodiment provides that the angle relative to the center axis of the lip section by which the lip section increases to its free outlet has a certain size, however, measures at most 25 degrees and preferably at most 15 degrees. Such a moderate increase of the lip section has been shown to be favorable.

In the scope of a different preferred embodiment it is provided that the lip section is designed as a flat passage whose width B which can be flowed through is significantly larger than its height H which can be flowed through. One talks of "significantly larger" in the sense of the invention when the ratio is at least 2.5 to 1, preferably at least 3 to 1 and ideally at least 4 to 1.

Preferably it is such that the height H at least marginally increases in the direction from the root up to the outlet of the lip section, typically by at least 2%.

In the scope of a particularly preferred embodiment it is provided that the lip section, measured from the internal side of the wall, has a width MB which can be flowed through in a first direction of $\geq 2.5$ mm and $\leq 25$ mm and/or in the general case $\leq 20$ mm, even more preferably between $\geq 3$ mm and $\leq 10$ mm. On the external side of the wall the lip has a size which is double the wall thickness, i.e. a size which is larger by at least 1.4 mm and at most 2.5 mm.

Also particularly preferred is the embodiment in which the outlet, measured from the internal side of the wall, has a height H which can be flowed through in a second direction which is perpendicular to a first direction of from $\geq 0.4$ mm and $\leq 2.5$ mm, preferably of from $\geq 0.4$ mm and $\leq 1.5$ mm, even more preferably of $\leq 1.1$ mm. For the size of the external side of the wall the above-mentioned also is true.

Such an applicator design is exceptionally slender and for this reason is very well suited for the precise dispensing.

In the scope of a different preferred embodiment it is provided that the lip section (with regard to its longitudinal axis which essentially corresponds to its fluid conveying direction) branches off at an angle of 15 degrees up to 90 degrees and preferably at an angle of 15 degrees up to 55 degrees or at 50° relative to the center axis of the closure piece which in the general case corresponds to the center axis of the supply container. Such a design allows a particularly practical handling of the applicator. In particular on the application of the applicator occurring on a needle or a cartridge it is not required to tilt the needle or the cartridge too strongly to be able to dispense or to even tilt it so far so that fluid permanently runs into the region of the bristle stock.

In a possible embodiment the lip section has a length of $\geq 70$ mm and preferably of $\geq 90$ mm from its root up to its outlet (calculated without a bristle stock), wherein the length is preferably limited and at the same time is then $\leq 160$ mm or ideally $\leq 140$ mm. Such a long and preferably slender lip section design under consideration of the above-mentioned width and height values simplifies the application in certain cases, as the dispensing apparatus does not have to be brought close to the face, but can be held at a certain distance from the face. This also allows the application to be perceived as being more pleasant.

Preferably, the closure piece has a locking section for fixing with a return in the lip or the mixer of a dispensing apparatus. Such a fine applicator, as has been discussed in the scope of the invention, can typically be mounted significantly easier at the dispensing apparatus in that it is fixed there rather than having a screw cap molded at the applicator.

In the scope of a preferred embodiment it is provided that the closure piece has a circumferential surface, which is intended to be elastically pretensioned against a complementary surface at the dispensing apparatus in the mounted state in an essentially radial direction. Thus, such a circumferential surface is designed such that on insertion of the applicator into the outlet (e.g. lip, needle, mixer) of the dispensing apparatus this is elastically tensioned with regard to the dispensing apparatus, whereby a seal is produced.

Preferably the applicator and/or its closure piece has an abutting surface perpendicular to its longitudinal axis. This abutting surface is intended to lie against a complementary surface of the dispensing apparatus in the mounted state. Preferably, however, not necessarily, also an elastic pretensioning and/or pre-stressing arises at this point, in particular in an axial direction.

Ideally the applicator is designed as opaquely transparent. This means that the applicator is transparent such that it can be recognized from the outside whether fluid is flowing through it. The user can then see how the fluid slowly moves through the lip section up to its outlet. This prevents, in particular for such a fine applicator as is under consideration in the scope of the invention that the user initially dispenses too much fluid under the impression "nothing is happening" following which, after a small time delay, finally an increased amount of fluid exits the outlet.

In the scope of a particularly preferred embodiment it is provided that, for guiding the fluid to the outlet of the lip section, the inner lying passage of the applicator is formed by two pushers mutually engaging one another of which one preferably is introduced locally into an opening of the other. Such a design, which leaves corresponding traces at the applicator, has significant advantages from a manufacturing point of view. As the complete component can be manufactured by injection molding. In this respect a large pusher is inserted from the side of the applicator which is intended for the connection to the dispensing apparatus. A smaller pusher is then inserted from the outlet side of the lip section into this, is incident at the first mentioned pusher and finally interacts in a complementary opening of the first mentioned pusher.

Figure 6:
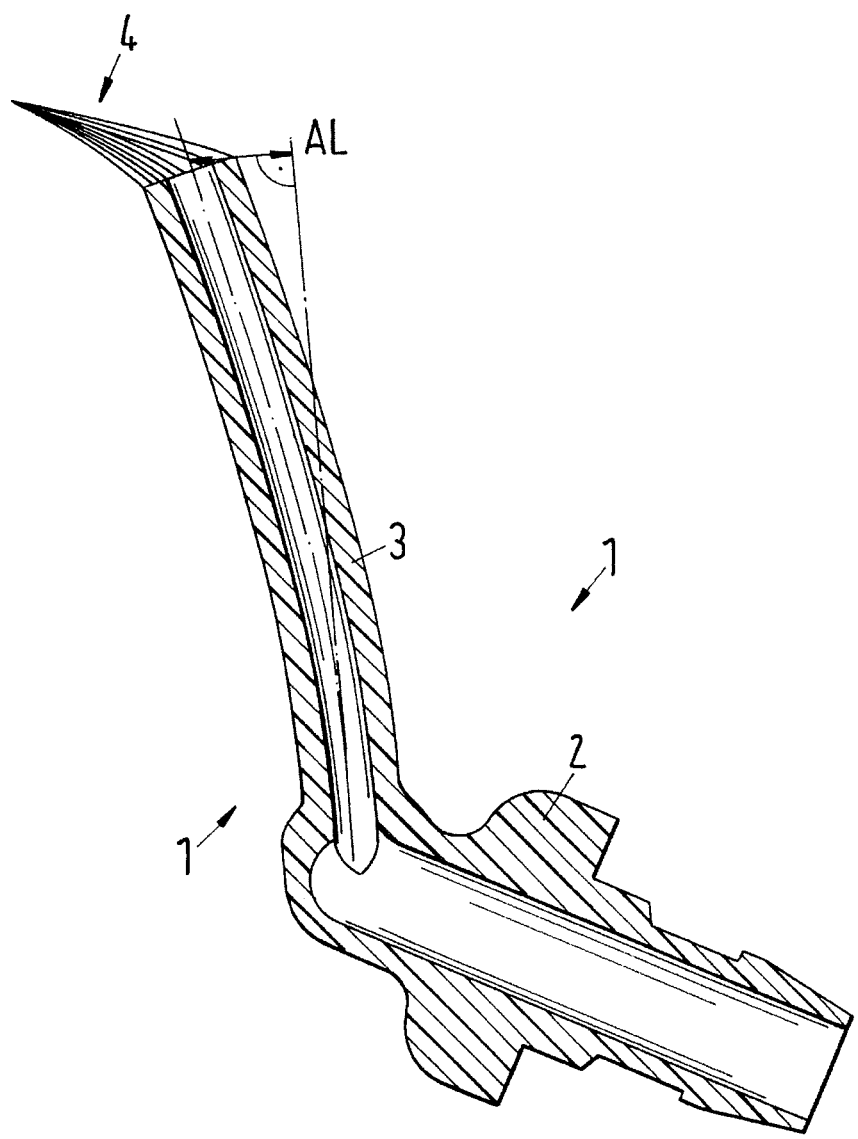
Figure 7:
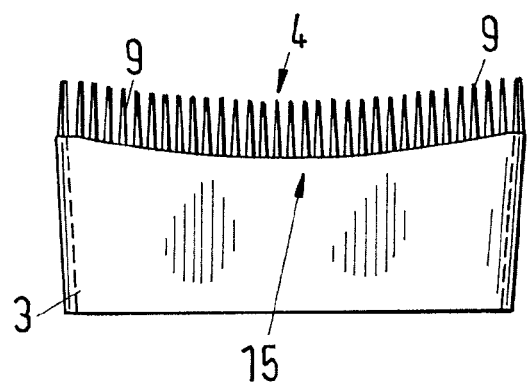

Further advantages, design possibilities, advantageous measures and modes of operation of the applicator in accordance with the invention result from the embodiment described in the following with the aid of a few drawings and from the dependent claims. In the drawings there is shown:

FIG. 1 a side view of an embodiment of an applicator in accordance with the invention;

FIG. 1*a* the same first embodiment as shown in FIG. 1, but illustrated on a 1:1 scale;

FIG. 2 a view of the applicator shown in FIG. 1 from the front;

FIG. 3 a perspective view of the applicator shown in FIGS. 1 and 2, but shown at a different scale as that of FIGS. 1 and 2;

FIG. 4 a section through the applicator in accordance with the invention in accordance with FIG. 1;

FIG. 5 a further section through the lip section of the applicator shown in FIG. 4, like FIGS. 4 and 5 they are shown at different scales, but both have a scale larger than that of FIGS. 1 to 3;

FIG. 6 an applicator in accordance with one of the previous drawings which is deformed under the influence of forces present on the application.

FIGS. 7-10 a second embodiment shown in a plurality of different perspectives in which the outlet is characterized by a convex curvature.

FIGS. 11-14 a third embodiment shown in a plurality of different perspectives in which the lip section is chambered at least at the outlet.

FIGS. 15-18 a fourth embodiment shown in a plurality of different perspectives in which the outlet is characterized by its concave curvature and/or convexity.

It should initially be noted that the bristles shown in the embodiments are preferably made from one material, this means made from one piece with the bristle stock and/or with the global applicator on injection molding. In this respect the bristle-shaping passages are vented so effectively and the melt is injected into the bristle-shaping passages at such a high pressure that a significant molecular orientation in the direction of the longitudinal axis of the bristle is set within each of the bristles. The bristles injection molded in such a manner in this respect behave very similar to a filament and/or to a stretched filament. Precisely this enables such a fine and yet resistant bristle to be manufactured as is required by the invention.

Where applicable, the bristles can also be manufactured in the so-called 2-K-process in that, for example, a perforated bristle support (which can be an integral component of the overall applicator) is initially manufactured through whose perforations the bristles are then sprayed in a second step. The points of view described above in the previous paragraph are also considered hereby.

FIG. 1 shows the applicator 1 in accordance with the first embodiment in large magnification while the applicator 1 forming this first embodiment is illustrated on a 1:1 scale in FIG. 1*a*. As the applicator is determined for use as a dental applicator it is designed particularly fine.

In the following reference is made to an applicator particularly relevant for practice in the field of dentistry, a dental applicator. The use as a dental applicator enables the exact, areal and thin-layered dispensing of fluid substances onto teeth or the dental sections of the patient. The dental applicator is placed at the outlet of the dispensing apparatus which includes, for example, a needle, a double needle or at least one cartridge. In the case of a one-component system the outlet of the dispensing apparatus is typically formed by a lip, a nozzle or a needle, in the case of a two-or multi-component system, the outlet of the dispensing apparatus is typically a static mixer which includes a mixing tube at whose end the two or more components exit as a homogenous mixed-through substance.

Beside the application in the field of dentistry, further fields of application relevant for practice are (industrial) bonding, in which one or more multi-component adhesives have to be applied to a predefined surface.

A closure piece 2 can easily be recognized with reference to FIG. 1, which includes a tube section 5 and a barb 6 to be connected in a form-matching manner to a corresponding outlet of the dispensing apparatus or a corresponding connection coupling for a dispensing apparatus. As can clearly be recognized a lip section 3 follows the closure piece 2. The lip section supports a bristle stock 4 at its distal end, this means at the end remote from the closure piece 2. The bristle stock is preferably exclusively composed of a number of essentially equal length bristles.

The closure piece has a circumferential surface 8 which is intended to be introduced into the outlet of the dispensing apparatus at an elastic pretensioning and to at least, additionally seal the barb 6. The barb also seals. For this purpose it has a barb sealing surface 6*a*. Furthermore, an attachment surface 7 is provided at an end face of the closure piece 2 which is placed against the face of the outlet of the dispensing apparatus.

The longitudinal axis L1 of the closure piece and the longitudinal axis L2 of the lip section can also be easily recognized. At the same time both longitudinal axes are also the longitudinal axis of the respective passage in the lip section 3 and the closure piece 2. As can be seen, the longitudinal axes meet in the region of the point at which the lip section 3 passes over into the closure piece 2.

FIG. 3 emphasizes the dimensions of the applicators in accordance with the invention, in accordance with the first embodiment with the aid of the outlet width MB, this means the length of the two longest walls bounding the outlet. As one can see, the applicators in accordance with the invention are designed as very compact with regard to their intended application, for example as dental applicators. For this embodiment, it is true that: 2.5 mm≤MB≤12 mm. Preferably it is also true that 2.5 mm≤MB≤8 mm.

As one can see, the lip section 3 projects at an angle α oblique from the closure piece 2. In this specific case the applicator has a projection AK of approximately 12.5 mm; generally one can say that the applicators in accordance with the invention should have a projection AK of between 5 mm and 20 mm, essentially preferably between 9 mm and 16 mm.

At the same time the applicator has a construction height BH of approximately 15.5 mm, it can generally can be held that the applicators in accordance with the invention should have a construction height of 8 mm to 18 mm, preferably of 10 mm to 16 mm.

FIG. 4 illustrates the so-called measure of the lip length TL. For applicators, which are placed onto a dispensing apparatus, and are used in the area of the mouth, it is advantageous when the user does not have to guide the supply chambers of the dispensing apparatus directly to or into the mouth which could be considered as being unpleasant. For this reason the lip length TL of ≥8 mm should be true. Preferably also TL ≥10 mm is true, ideally TL ≥12 mm is true.

FIG. 2 shows the applicator shown in the Figure from the front. For the first time one can see how the outlet 10 of the applicator is completely bounded by the field of bristles and/or the bristle stock 4. One can already see from this Figure that the bristle field is composed of a single row of bristles 9 which are "placed" at the end face of the lip section bounding the outlet 10.

Further details are seen in FIG. 3. In particular one can see that the bristles 9 are indeed placed in a row around the end face in the present example. The bristles bound the outlet 10. However, the bristles do not all absolutely project in a row, but are alternatively displaced with respect to one another. In this respect the displacement respectively amounts to approximately half a bristle diameter (in the foot region of the bristle). Hereby the bristle stock has a tendency to be more stable overall, for example, less sensitive to kinks and a little more solid in its application characteristics for equal bristle diameters. It can generally be held that the displacement should preferably be in the region of between ¼ of the bristle diameter and approximately ¾ of the bristle diameter and/or preferably be only ¾ of the bristle diameter. An even larger bristle separation than the one mentioned allows the development of too large free spaces between the individual bristles and for this reason influence the result of the application while even smaller bristle separation distances than the one mentioned have the effect that neighboring bristles easily stick to one another under the influence of the fluid and for this reason also influence the result of the application. This rule is also true when not a single row bristle stock, but a multi row bristle stock is provided.

At the same time one can see that the bristle diameter in the foot region is smaller than the wall thickness of the lip section directly at its distal end. In the individual case, this means that also two or three rows of bristles can be placed around the end face of the lip section 3 bounding the outlet 10 in contrast to what is shown in FIG. 3. However, this is not preferred as the boundary of the lip section 3 can then threaten to become too thick.

Further details can be recognized with regard to FIG. 4 which shows a section of the applicator illustrated in FIG. 1.

The closure piece 2 with its tube section 5, its barb 6 and its circumferential surface 8 provided, preferably radially pre-stressed for the sealing interaction with the outlet of the dispensing apparatus as well as its end face abutting surface 7 which in accordance with its intended use is intended to be brought into contact at a corresponding end face of the outlet of the dispensing apparatus can clearly be seen. Naturally the applicator can also be designed for attachment to a coupling unit which is then coupled to the outlet of the dispensing device.

As can also be clearly recognized, the closure piece 2 has a stiffening ring 13 in the longitudinal direction in the form of a rib of approximately 1.5 mm to 3 mm width surrounding the circumferential direction. This region represents the most solid region of the applicator 1 and preferably serves for the handling of the applicator at least in the course of its production, this means for pressing on and preferably locking the applicator at the outlet of the dispensing apparatus and/or for the release. This stiffening ring simultaneously supports the applicator very well with regard to the end face of the outlet of the dispensing apparatus, as soon as, for example, a bending moment is transferred to the closure piece 2 via the lip section 3, the closure piece 2 has to compensate the bending moment and deflect it into the outlet of the dispensing apparatus. In the specific case the length VL of the closure piece amounts to approximately 8 mm, it can generally be held that the length of the closure piece should lie between 5 mm and 15 mm, preferably lie between 6 mm and 11 mm.

The outer diameter RD of the tube section 5 which is intended for the insertion into the outlet of the dispensing apparatus amounts to 2.25 mm in the specific case. For dental applicators it can generally be held that this outer diameter should be smaller than or equal to 9 mm, preferably smaller than or equal to 7.5 mm. For other applications it can be favorable when the outer diameter lies between 1.8 mm and 5 mm or preferably still between 1.8 mm and maximally 3 mm. In the specific case the inner diameter ID of the passage section 11 reaching through the closure piece 2, which is designed as circularly round, amounts to up to 1.6 mm and preferably lies between 1.3 mm and 4 mm, especially between 1.3 mm and 2.6 mm. For dental applicators an inner diameter of at most 8 mm preferably of at most 7 mm is preferred.

It can also be clearly recognized with regard to FIG. 4 that the longitudinal axis of the individual bristles 9 runs essentially in parallel to the longitudinal axis L2 of the lip section. Furthermore, it can be seen that the bristles really do bound the outlet 10 in the novel state such that they do not protrude into the region of the outlet 10 or into the pre-space of the outlet 10.

The bristles are all of equal length in the present example. This is preferred for a bristle arrangement of only a single row, as otherwise the danger is relatively large that the longer of the bristles are supported too little by the neighboring bristles and for this reason kink off prematurely when different lengths of bristles are provided.

The bristle diameter BD can also be clearly recognized in the foot region. In some cases this is ≤0.8 mm, however, preferably lies significantly beneath that, namely at ≤0.5 mm or preferably even at ≤0.35 mm and/or ideally at ≤0.25 mm. In the specific case the length of 2.6 mm has been found to be ideal as a bristle length BL, generally one can say that the bristle length BL should lie between 1.9 mm and 4.5 mm.

By comparison of FIGS. 4 and 5 one can relatively clearly see that the lip section 3 is designed as a flat passage having a width B and a height H. The width B at this flat passage significantly increases from the root of the flat passage up to its outlet, preferably the width B is more than doubled, this is generally true. In ideal cases the width B can even be tripled. As can only be recognized with difficulty with regard to FIG. 4 the height H of the flat passage also increases from the root of the lip section 3 to its outlet. Responsible for this is the angle γ, this means the fact that the walls which form the internally lying passage 12 of the lip section shown in the sectional plane perpendicular to that of FIG. 4 are not one hundred percent parallel, but diverge from the root of the lip section by about an angle γ of approximately 0.5 degrees. Very generally, it can be said that this angle γ should lie between 0.3 degrees and 3.5 degrees, preferably at most 2.5 degrees.

The wall thickness WS of the lip section preferably lies at approximately 0.4 mm, generally it can be held that wall thicknesses between 0.3 mm and approximately 0.6 mm are ideal.

As one can recognize with regard to FIG. 5 also the walls, which are oriented perpendicular to this sectional plane and bound the flat passage in the present case, are not parallel to one another, but diverge starting from the root by an angle β. This angle β amounts to approximately 13 degrees in the present case. It can generally be held that the angle β should lie between 7.5 degrees and 30 degrees, preferably ≤20 degrees and ideally ≤17.5 degrees.

As one can recognize quite clearly with regard to FIG. 5 the passage section 12 passing through the lip section 3 has a section 14 in the region of its root within which the internal cross-section of the passage section 12 remains the same in parts.

FIG. 5 also illustrates the doubled bristle separation DBA. In the present embodiment this amounts to approximately 0.6 mm, generally it can be held that the double bristle separation DBA should lie between 0.4 mm and 0.8 mm.

The applicator shown in this embodiment is made of LDPE (low density polyethylene). LDPE is a preferred material in this context which has ideal properties for such an applicator, in particular when this should be manufactured as a one-way applicator. Naturally, also other types of plastics are suitable for the manufacture of the applicator, for example PA (polyamide) or PP (polypropylene).

The applicator preferably used and shown in this embodiment is opaquely transparent. This means that the applicator is preferably so transparent that it can be recognized from the outside whether a fluid is flowing through the applicator and how much of the fluid flows through the applicator.

Its lip section is so elastic and/or so flexible that it can be moved in a type and manner as illustrated in FIG. 6, namely by an amount of at least AL ≥1 mm, preferably even by an amount AL of ≥2 mm, ideally by an amount of even ≥3 mm. Such an elasticity brings about a comfortable application behavior of the applicator particularly on use in the field of dentistry.

The lip section 3 is preferably flexible in at least one plane such that the outlet of the lip section can elastically yield resiliently under the influence of the forces present on application by an amount of at least 1.5 mm, preferably by at least 2 and ideally by at least 3 mm.

FIGS. 7 to 10 show illustrations of an end of the lip section which is designed in an alternative manner, thus a second embodiment. Such an end can be an integral component of the lip section 3 or also be initially designed as a separate attachment which is placed onto a corresponding coupling section of a lip.

The lip section, to which this end belongs and also the rest of the associated applicator are not illustrated by form of a drawing, however, are designed precisely like the lip section and its applicator previously described. The previously mentioned is therefore valid without restriction also for this embodiment, with the exception of those differences to which explicit references are made in the following.

The outlet region of the lip section shown in the present example has a concave, preferably sickle-shaped curvature 15, this means a curvature which represents an impression in the region of the center of the outlet. Expressed in slightly different words, it is such that the opening of the outlet is spanned by a (imagined) concave surface.

The bristle stock also has this concave curvature, illustrated in the Figure of the embodiment as sickle-shaped and is preferably exclusively composed of a number of substantially equal-length bristles. The lip section is approximately as wide as a human eye at its outlet end (distal) side and with its sickle-shaped curvature is matched well to the run of the human eye lid and/or its eyelash arc. Due to this, this lip section is particularly predisposed to form an internally fed mascara applicator or an applicator for applying a different substance onto the eye lid.

In particular for such an applicator it is naturally important that the applicator is indeed wide enough to be able to treat the overall eyelash stock of an eye lid, but that it is otherwise very fine. For this reason, the outlet region of the lip section is designed such that it forms a flat passage directly in the region of the outlet opening whose internal width B is at least eight times as large as its internal height H in the present case.

Figure 8:
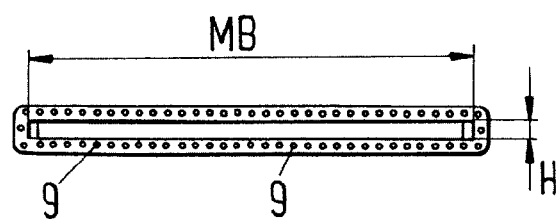
Figure 9:
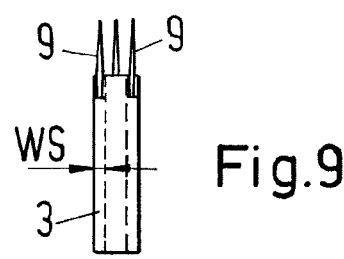
Figure 10:
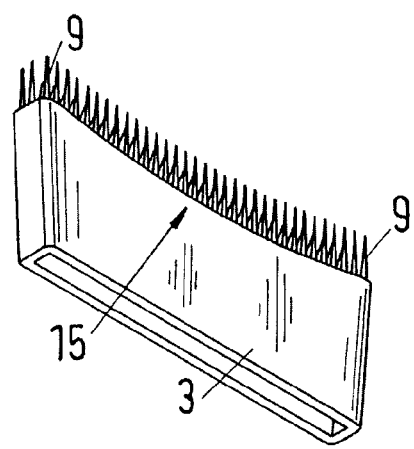
Figure 11:
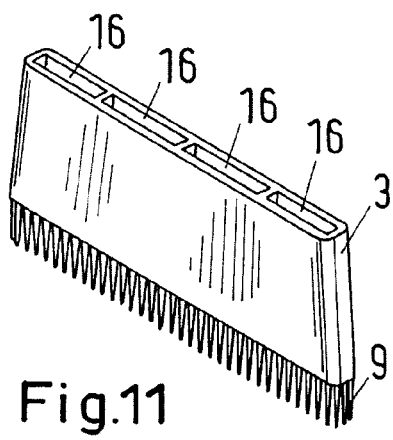

FIG. 8 emphasizes the dimensions of the applicators in accordance with the invention of the second embodiment with the aid of the outlet width MB, this means the two longest walls bounding the outlet. As one can see the applicators in accordance with the invention are also designed quite fine in the present case due to their intended use as applicators. In accordance with the invention MB is preferably ≤25 mm for this embodiment.

In this respect it is remarkable that the gap height H is significantly smaller than the outlet width MB for the embodiments in accordance with the pattern of the second embodiment. It is preferably true that MB is larger than H at least by factor of 8, preferably still by at least a factor of 10. Such a relation is advantageous as, on the one hand, it indeed allows a fluid to be applied in one working step over a wide width and, on the other hand, also increases the through flow resistance of the lip section so far that only the actually required amount of fluid exits.

Ideally such an applicator is only provided with a single row of bristles all round, as otherwise it would be too bulky and frequently also no good comb effect would enfold. Preferably, these bristles project along the border from which they extend respectively in one alignment as can be seen with regard to the Figures.

The FIGS. 11 to 14 show illustrations of an end of a lip section which is alternatively designed, thus a third embodiment. Such an end can be an integral component of the lip section or also be designed as an attachment which is placed onto a corresponding coupling section of a lip.

The lip section to which this end belongs and also the remainder of the associated applicator are not illustrated in the drawing, however, they are designed precisely like the lip section and its applicator described with reference to FIGS. 2 to 6. The statements made with regard to that lip section are also valid without restriction for this embodiment, with the exception of those differences which will be explicitly mentioned in the following. For the sake of good order it should also be noted that the lip section illustrated in FIGS. 11 to 14 can naturally also have a concave curvature as is described above with regard to FIGS. 7 to 10.

At least the outlet region of the lip section shown in the present case is divided into a plurality of chambers 16 and/or "supply lines" preferably lying "narrow side next narrow side".

As it forces a uniform through-flow, such a "chambering" generally promotes the regularity of the dispensing and stabilizes the narrow flow cross-section of the lip section. The latter is important, in particular when the lip section is designed to be elastically resilient as is described above in connection with the first embodiment.

Generally it is true that a division into too many chambers 16 is not sensible, if only to counteract a possible congestion and for reasons of hygiene. For this reason the number of chambers 16 should be limited to a maximum of 6 parallel chambers, preferably to a maximum of 4 parallel chambers.

Figure 12:
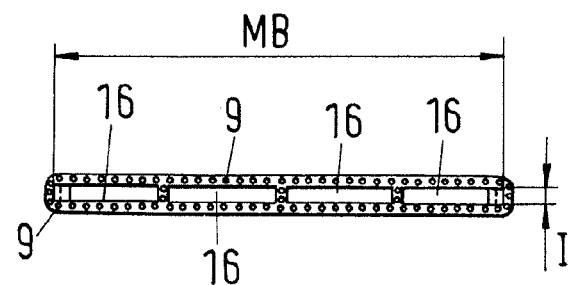
Figure 13:
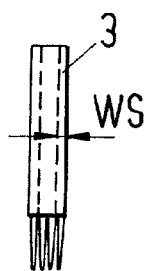
Figure 14:
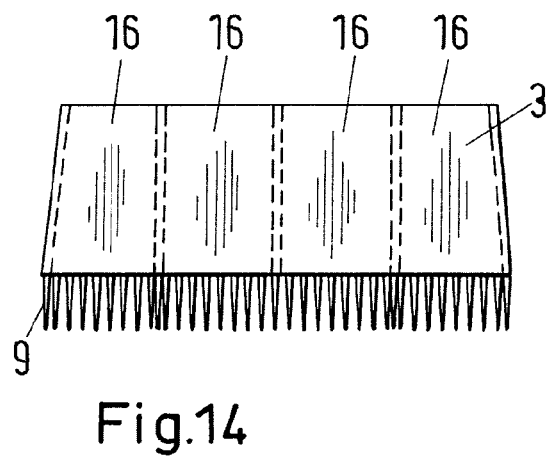
Figure 15:
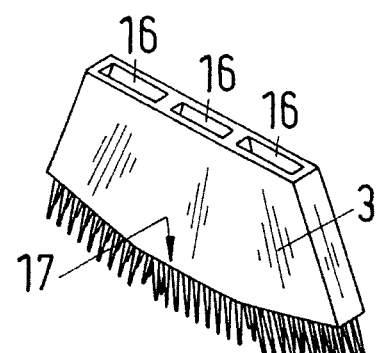
Figure 16:
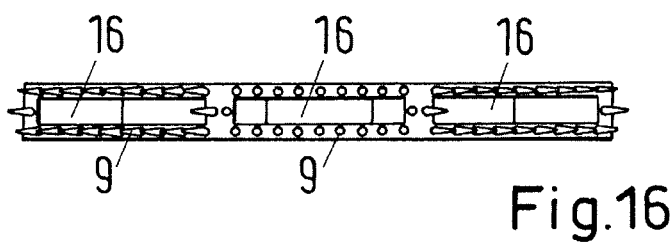
Figure 18:
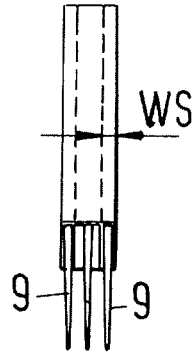
Figure 17:
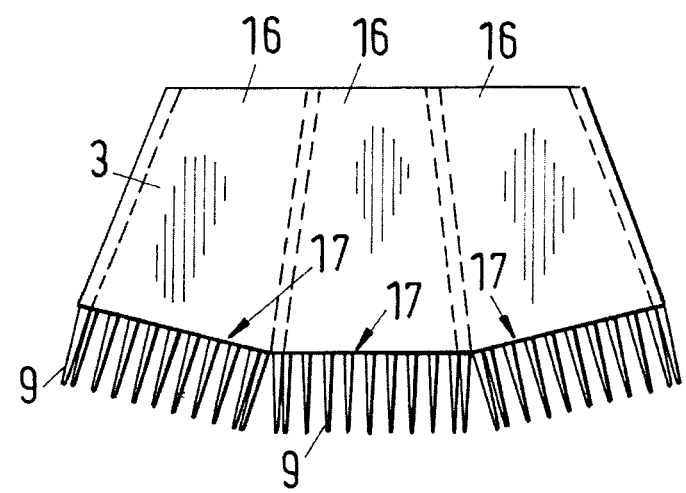

FIG. 12 emphasizes the dimensions of this third embodiment of the applicators in accordance with the invention using the aid of the outlet width MB, this means the two longest wall banding the outlet. As one can see the applicators in accordance with the invention are also carried out quite compact and small in the present case with regard to their intended application as applicators. In accordance with the invention it is true for this embodiment that MB is preferably: ≤25 mm.

In this respect it is remarkable in turn that the gap width H is significantly smaller than the outlet width MB in the embodiments in accordance with the pattern of the second embodiment. It is preferably true that MB is larger than H by a factor of 8, preferably still by at least a factor of 10. Such a relation is advantageous as it, on the one hand, allows to apply the fluid in one working step over a large width and, on the other hand, also increases the flow-through resistance of the lip section so far that only the required amount of fluid exits.

The FIGS. 15 to 18 show illustrates an end of a lip section, which is alternatively designed, thus a fourth embodiment. Such an end can be an integral component of the lip section or be designed as an attachment which is placed onto a corresponding coupling section of a lip.

The lip section, to which this end belongs and also the rest of the associated applicator are not illustrated in the drawing, but they are designed precisely like the lip section and the applicator described with reference to FIGS. 2 to 6. For this reason, the statements made with regard to that lip section are also valid without restriction for this embodiment with the exception of those differences which will be explicitly indicated in the following.

The outlet region of the lip section shown in the present case has a, in the broadest sense, convex and/or round design 17, this means a design which projects outwardly in the region of the center of the outlet. Expressed in slightly different words it is such that the opening of the outlet is spanned, by a (taught) in the broadest sense round surface.

This has the effect that the bristles of the bristle stock project in different directions, at least in groups, preferably in the shape of a fan. In this way and manner it is simpler to only bring about a contact between a part of the bristle stock with the party to be treated. This can simplify a selective dispensing, for example, of a colored lip cosmetic or of a gloss lip cosmetic or of a glue which should only cover a precisely intended surface.

Preferably also a chambering is provided for this embodiment, as is described with reference to the third embodiment in accordance with FIGS. 11 to 14. The statements made with regard to those Figures is therefore also true in the present case.

The statements made with regard to the outlet width MB and the relation of MB and H with regard to the second and third embodiment is also valid in the present case.

The invention claimed is:

1. An internally fed applicator for applying a fluid comprising:
    a closure piece configured to fix the applicator to a dispensing apparatus;
    an internally hollow lip section connected to the closure piece in a fluid conducting manner, the lip section comprising an outlet at a distal end, the outlet having an outlet width and a gap height, the gap height being significantly smaller than the outlet width, and the lip section further comprising a flat passage having a width, the width of the flat passage significantly increasing from a root of the flat passage up to the outlet; and
    a bristle stock comprising bristles, the bristle stock being supported at the distal end of the lip section, the bristle stock further being made of bristles injection molded and integrally formed with the lip section, each bristle having a diameter of at most 0.8 mm, and the supplied fluid being delivered via the lip section to the bristle stock.

2. The applicator of claim 1, wherein the bristle stock completely surrounds the outlet.

3. The applicator of claim 1, wherein at least a predominant number of the bristles forming the bristle stock has a bristle center line extending essentially parallel to a center line of the lip section.

4. The applicator of in of claim 1, wherein at least one border of the lip section has a single row of bristles, the bristles standing adjacent one another along the border.

5. The applicator of claim 1, wherein the bristles do not protrude into or in front of an exit cross section of the outlet of the lip section.

6. The applicator of claim 1, wherein the bristles have a generally round cross section over their total length.

7. The applicator of claim 1, wherein a lateral surface of the bristles is conical having a cone angle of between 0.3° to 2.5° with respect to the longitudinal axis of the respective bristles.

8. The applicator of claim 1, wherein at least a predominant number of the bristles has a bristle length of at most 4.5 mm.

9. The applicator of claim 1, wherein a bristle diameter at a bristle root is smaller than a wall thickness of a wall supporting the bristles in a region of the bristle root.

10. The applicator of claim 1, wherein a diameter or a width of the lip section increases in at least one plane from the closure piece to the outlet.

11. The applicator of claim 1, wherein
the outlet has a width configured to be flowed through in a first direction ranging from ≥3 mm and ≤16 mm.

12. The applicator of claim 1, wherein
the lip section branches off at an angle of 15° to 90° relative to a center axis of the closure piece with respect to a longitudinal axis of the lip section the longitudinal axis of the section corresponding to a fluid conveying direction.

13. The applicator of claim 1, wherein
the lip section is flexible in at least one plane such that the outlet of the lip section is configured to elastically resiliently yield under the influence of the forces arising on the application by an amount of at least 1.5 mm.

14. The applicator of claim 1, wherein
the applicator is made of a soft, tough and flexible material.

15. The applicator of claim 1, wherein
a tube section of the closure piece provided for a sealing insertion into a container neck has an outer diameter ≤9mm.

16. The applicator of claim 1, wherein
all of the bristles forming the bristle stock have a bristle center line extending essentially parallel to a center line of the lip section.

17. The applicator of claim 1, wherein
all borders of the lip section have a single row of bristles standing adjacent one another along each respective border.

18. The applicator of claim 1, wherein
the bristles do not substantially protrude into or in front of an exit cross section of the outlet of the lip section.

19. The applicator of claim 1, wherein
at least a predominant number of the bristles have a bristle length of at most 3.4 mm.

20. The applicator of claim 1, wherein
at least a predominant number of the bristles have a bristle length of at most 2.9 mm.

21. The applicator of claim 1, wherein
all of the bristles have a bristle length of at most 4.5 mm.

22. The applicator of claim 1, wherein
all of the bristles have a bristle length of at most 3.4 mm.

23. The applicator of claim 1, wherein
all of the bristles have a bristle length of at most 2.9 mm.

24. The applicator of claim 1, wherein
the outlet has a width configured to be flowed through in a first direction ranging from ≥3 mm and ≤8 mm.

25. The applicator of claim 1, wherein
the outlet has a width configured to be flowed through in a first direction ranging from ≥3 mm and ≤6 mm.

26. The applicator of claim h wherein
the lip section branches off at an angle of 15° to 50° relative to the center axis of the closure piece with respect to a longitudinal axis of the lip section, the Longitudinal axis of the lip section corresponding to a fluid conveying direction.

27. The applicator of claim 1, wherein
the lip section is flexible in at least one plane such that the outlet of the lip section is configured to elastically resiliently yield under the influence of the forces arising on the application by an amount of at least 2 mm.

28. The applicator of claim 1, wherein
the lip section is flexible in at least one plane such that the outlet of the lip section is configured to elastically resiliently yield under the influence of the forces arising on the application by an amount of at least 3 mm.

29. The applicator of claim 1, wherein
the applicator including the bristles is made of a soft, tough and flexible material.

30. The applicator of claim 1, wherein
the tube section of the closure piece provided for a sealing insertion into a container neck coupling has an outer diameter ≤75 mm.

* * * * *